(12) United States Patent
Gaudin (10) Patent No.: US 9,492,788 B2
(45) Date of Patent: Nov. 15, 2016

(54) METHOD FOR DIAGNOSING A SELECTIVE CATALYTIC REDUCTION CATALYST

(75) Inventor: Bruno Gaudin, Chozeau (FR)

(73) Assignee: Volvo Construction Equipment AB, Eskilstuna (SE)

(*) Notice: Subject to any disclaimer, the term of this patent is extended or adjusted under 35 U.S.C. 154(b) by 137 days.

(21) Appl. No.: 14/388,373

(22) PCT Filed: Mar. 29, 2012

(86) PCT No.: PCT/SE2012/000047
§ 371 (c)(1),
(2), (4) Date: Oct. 1, 2014

(87) PCT Pub. No.: WO2013/147653
PCT Pub. Date: Oct. 3, 2013

(65) Prior Publication Data
US 2015/0151251 A1 Jun. 4, 2015

(51) Int. Cl.
*B01D 53/94* (2006.01)
*G01N 33/00* (2006.01)
(Continued)

(52) U.S. Cl.
CPC ....... *B01D 53/9495* (2013.01); *B01D 53/9431* (2013.01); *F01N 3/208* (2013.01);
(Continued)

(58) Field of Classification Search
CPC ............ B01D 2251/2062; B01D 2255/80; B01D 2257/404; B01D 53/9409;
(Continued)

(56) References Cited

U.S. PATENT DOCUMENTS 5,369,956 A * 12/1994 Daudel .............. B01D 53/8696
60/276
9,144,772 B2 * 9/2015 Pfister ................ B01D 53/9495
(Continued)

FOREIGN PATENT DOCUMENTS

EP 2333261 A1 6/2011

OTHER PUBLICATIONS

International Search Report (Nov. 16, 2012) for corresponding International Application PCT/SE2012/000047.
(Continued)

*Primary Examiner* — Maureen Wallenhorst
(74) *Attorney, Agent, or Firm* — WRB-IP LLP (57) ABSTRACT

A method for diagnosing a selective catalytic reduction (SCR) catalyst of an exhaust aftertreatment system of an internal combustion engine includes ensuring that a SCR catalyst NH3 storage level is substantially below the current maximal NH3 storage capacity of the SCR catalyst, initiating over-injection of reductant by the injector, stopping reductant injection upon registering, by the exhaust gas sensor, an increasing NOx+NH3 emission level and an NOx+NH3 emission level exceeding a predefined threshold value, and when the reduction injection is stopped recording an output signal of the exhaust gas sensor until an indication of a minimal or negligible SCR catalyst NH3 storage level is determined, and calculating a SCR catalyst NH3 storage capacity on the basis of the recorded output signal.

19 Claims, 2 Drawing Sheets

(51) Int. Cl.
  *F01N 3/20* (2006.01)
  *F01N 9/00* (2006.01)
  *F01N 11/00* (2006.01)
  *F01N 3/10* (2006.01)
  *F01N 13/00* (2010.01)

(52) U.S. Cl.
  CPC ............... F01N 9/00 (2013.01); F01N 11/00 (2013.01); G01N 33/0037 (2013.01); G01N 33/0067 (2013.01); *B01D 2251/2062* (2013.01); *B01D 2255/80* (2013.01); *B01D 2257/404* (2013.01); *F01N 3/106* (2013.01); *F01N 13/009* (2014.06); *F01N 2430/00* (2013.01); *F01N 2550/02* (2013.01); *F01N 2560/021* (2013.01); *F01N 2560/026* (2013.01); *F01N 2560/14* (2013.01); *F01N 2900/0418* (2013.01); *F01N 2900/1402* (2013.01); *F01N 2900/1614* (2013.01); *F01N 2900/1616* (2013.01); *Y02T 10/24* (2013.01); *Y02T 10/47* (2013.01); *Y10T 436/175383* (2015.01)

(58) Field of Classification Search
  CPC ............ B01D 53/9413; B01D 53/9431; B01D 53/9495; B01D 53/9436; F01N 11/00; F01N 13/009; F01N 2430/00; F01N 2550/02; F01N 2560/021; F01N 2560/026; F01N 2560/14; F01N 2900/0418; F01N 2900/1402; F01N 2900/1614; F01N 2900/1616; F01N 3/106; F01N 3/208; F01N 9/00; G01N 33/0037; G01N 33/0054; G01N 33/0067; Y02T 10/24; Y02T 10/47; Y10T 436/12; Y10T 436/17; Y10T 436/171538; Y10T 436/175383; Y10T 436/177692; Y10T 436/179228
  USPC .......... 436/37, 55, 106, 108, 113, 116, 118; 423/212

See application file for complete search history.

(56) References Cited

U.S. PATENT DOCUMENTS

| | | | |
|---|---|---|---|
| 2005/0282285 A1* | 12/2005 | Radhamohan | B01D 53/90 436/55 |
| 2009/0301068 A1* | 12/2009 | Fujita | F01N 3/208 60/286 |
| 2010/0028230 A1* | 2/2010 | Gady | F01N 3/208 423/239.1 |
| 2010/0180576 A1 | 7/2010 | Wang et al. | |
| 2010/0326051 A1 | 12/2010 | Busch et al. | |
| 2011/0131956 A1 | 6/2011 | Yasui et al. | |
| 2011/0192148 A1 | 8/2011 | Yasui | |
| 2011/0296905 A1 | 12/2011 | Bastoreala et al. | |

OTHER PUBLICATIONS

International Preliminary Report on Patentability (Feb. 13, 2014) for corresponding International Application PCT/SE2012/000047.
European Search Report (Dec. 2, 2015) for corresponding European App. 12 872 355.8.

* cited by examiner

METHOD FOR DIAGNOSING A SELECTIVE CATALYTIC REDUCTION CATALYST

BACKGROUND AND SUMMARY

This invention relates, according to an aspect thereof, to a method for diagnosing a selective catalytic reduction (SCR) catalyst of an exhaust aftertreatment system of an internal combustion engine, wherein said exhaust aftertreatment system comprises a SCR catalyst, an reductant injector arranged upstream of said SCR catalyst for injecting a reductant into an exhaust gas, and an exhaust gas sensor arranged downstream of said SCR catalyst, which sensor being cross-sensitive to nitrogen oxide (NOx) and ammonia (NH3) present within the exhaust gas leaving said SCR catalyst.

The invention is applicable for example on vehicles provided with SCR catalyst, such as working machines within the field of industrial construction machines, in particular wheel loaders and articulated haulers, but also other vehicles such as a truck or bus comprising a compression ignition engine configured to be powered with diesel or similar fuel types.

Present regulatory conditions in the automotive market have led to an increasing demand to improve fuel economy and reduce emissions in present vehicles. These regulatory conditions must be balanced with the demands of a consumer for high performance and quick response for a vehicle.

A diesel engine has a high efficiency of and is one of the best converters of fossil energy. NOx emission concentration is dependent upon local oxygen atom concentration and the local temperature. Said high efficiency is however only possible at an elevated combustion temperature at which high NOx levels are inevitable. Moreover, a suppression of NOx formation by internal means (air/fuel ratio) has the tendency to cause an increase in particulates, known as the NOx-particulates trade off, Furthermore, an excess of oxygen in the exhaust gas from a diesel engine prevents the use of stoichiometric 3-way-catalyst technology for reduction of NOx as is used in gasoline engine cars from the late 80-ties.

Reducing the oxides of nitrogen (NO and NO2, referred to as NOx) and particulate matter (PM) in exhaust gases from a diesel engine has become a very important problem in view of the protection of environment and the saving of finite fossil energy supply.

Vehicles equipped with diesel or other lean burn engines offer the benefit of increased fuel economy, however, catalytic reduction of NOx emissions via conventional means in such systems is difficult due to the high content of oxygen in the exhaust gas. In this regard Selective Catalytic Reduction (SCR) catalysts, in which NOx is continuously removed through active injection of a reductant into the exhaust gas mixture entering the catalyst, are known to achieve high NOx conversion efficiency. Urea based SCR catalysts use gaseous ammonia as the active NOx reducing reductant. Typically, an aqueous solution of urea is carried on board of a vehicle, and an injection system is used to supply it into the exhaust gas stream entering the SCR catalyst where it decomposes into hydro cyanic acid (NHCO) and gaseous ammonia (NH3), which is then used to convert NOx.

However, in such systems, urea injection levels have to be very precisely controlled. Under-injection of urea may result in sub-optimal NOx conversion, while over-injection may cause tailpipe ammonia slip, In a typical urea-based SCR catalyst system, the amount of urea injected is in proportion to the exhaust gas NOx concentration that represents a trade-off between maximum NOX conversion and minimum ammonia slip.

NOx conversion efficiency of an SCR catalyst is improved in the presence of adsorbed ammonia within the SCR catalyst, wherein the level of adsorbed ammonia is denoted SCR catalyst ammonia storage level. NOx conversion efficiency is improved in a steady state condition by the ammonia buffer within the SCR catalyst. Moreover, NOx conversion efficiency is particularly improved during transient conditions by the ammonia buffer, when reductant injection may not follow the transient NOx emission level correctly. In this situation, adsorbed ammonia, within the SCR catalyst assures sufficient continuous NOx reduction to respect regulatory emission levels. However, if too much ammonia is stored in the catalyst under certain operating conditions, such as high temperatures, some of the stored ammonia in the catalyst may desorb and slip from the catalyst or to be oxidized to NOx and thereby reducing the overall NOx conversion efficiency.

For the purpose of efficient and regulatory fulfilling NOx emission reduction, it is desirable to determine the SCR catalyst performance and condition, and in particular the NH3 storage capacity of the SCR catalyst.

Document U.S. 2010/0326051 shows an operating and diagnostic method, wherein the total converted ammonia amount which is stored in the SCR catalytic convener may be calculated. This diagnostic method however suffers from relatively low accuracy with respect to the true storage capacity of the SCR convener.

There is thus a need for an improved method for diagnosing a SCR catalyst removing the above mentioned disadvantages.

It is desirable to provide an inventive method for diagnosing a SCR catalyst where the previously mentioned problem is at least partly avoided.

The invention concerns, according to an aspect thereof, a method for diagnosing a selective catalytic reduction (SCR) catalyst of an exhaust aftertreatment system of an internal combustion engine, wherein said exhaust aftertreatment system comprises a SCR catalyst, an reductant injector arranged upstream of said SCR catalyst for injecting a reductant into an exhaust gas, and an exhaust gas sensor arranged downstream of said SCR catalyst, which sensor being cross-sensitive to nitrogen oxide (NOx) and ammonia (NH3) present within the exhaust gas leaving said SCR catalyst.

The inventive method comprises the steps of ensuring that a SCR catalyst NH3 storage level is substantially below the current maximal NH3 storage capacity of said SCR catalyst; initiating over-injection of reductant by said injector; stopping reductant injection upon registering, by said exhaust gas sensor, an increasing NOx+NH3 emission level and an NOx+NH3 emission level exceeding a predefined threshold value, and when the reduction injection is stopped recording an output signal of said exhaust gas sensor until an indication of a minimal or negligible NH3 storage level is determined; and calculating, a SCR catalyst NH3 storage capacity on the basis of said recorded output signal.

The inventive method provides improved accuracy of the calculated NH3 storage capacity of the SCR catalyst because the level of ammonia slip at begin of the recording of the output signal of said exhaust gas sensor is very small, and will therefore only distort the calculated NH3 storage capacity value to a minimal extent. This very small level of ammonia slip can be detected by the inventive method due to the careful preparation of the recording, namely ensuring that the level of stored ammonia is relatively low and subsequently initiating over-injection if reductant. An important aspect of the inventive method is early detection of ammonia slip, which occurs upon reaching a high level of ammonia storage in the SCR catalyst. It is known to install an additional ammonia sensor downstream of the SCR catalyst for detecting ammonia slip, but an additional ammonia sensor results in higher cost, more complex system with higher risk of malfunction. The early detection of ammonia slip is according to the invention accomplished by continuously monitoring the output signal from the exhaust gas sensor. No additional ammonia sensor is consequently required. The over-injection of reductant will lead to ammonia slip when the ammonia storage level is sufficiently high, but due to the initial low level of stored ammonia in the SCR catalyst, it can be established that the initial output signal of the exhaust gas sensor corresponds to the NOx emission level only, and that no ammonia slip distorts said NOx emission level. Knowing that the output signal of the exhaust gas sensor corresponds only to NOx emission, it can be concluded, that any increase in the output signal of the exhaust gas sensor must result from ammonia slip, based on constant NOx emission level entering the SCR catalyst, and constant exhaust gas temperature. Consequently, a very early detection of ammonia slip can be established, without the use of a dedicated ammonia sensor, thereby facilitating calculation of the SCR catalyst NH3 storage capacity with high level of accuracy.

Also, using an indication of a minimal or negligible NH3 storage level as end criteria of the output signal recording of the exhaust gas sensor further improves accuracy of the NH3 storage capacity calculation. The ammonia storage capacity calculation is based on the assumption that all ammonia in SCR catalyst have been converted, i.e. zero NH3 storage level. Evidently, if some amount of adsorbed ammonia still remains within the SCR catalyst, the calculated NH3 storage capacity will be distorted to a certain extent. Depending on SCR catalyst type, operating temperature, etc., the time to completely empty the SCR catalyst of ammonia may take relatively long time. A compromise between the accuracy of the calculated NH3 storage capacity and time for performing the diagnose is thus established. From above, it is clear that an indication of a minimal or negligible NH3 storage level will deliver a highly accurate calculation of the NH3 storage capacity of the SCR catalyst.

Knowing accurately the NH3 storage capacity of the SCR catalyst, not only can the reductant dosage level be controlled more optimally, but an indication of the status of the SCR catalyst is derived. As previously mentioned, high NH3 storage capacity of the SCR catalyst can to a greater extent convert transient NOx emission levels. Upon detecting a SCR catalyst with a relatively small NH3 capacity, this may indicate need of replacement or repair of the SCR catalyst.

The method may further comprise the step of providing the exhaust aftertreatment system with an additional exhaust gas sensor arranged upstream of said reductant injector, which additional exhaust gas sensor being configured to measure the level of NOx present within the exhaust gas entering said SCR catalyst. By providing a NOx-sensible sensor upstream and downstream of the SCR catalyst, the conversion efficiency can be directly determined, thereby facilitating improved and simplified control of reductant injection level, as well as continuous monitoring of the NOx emission conversion efficiency. Without the additional exhaust gas sensor the NOx emission level of the exhaust gas entering the SCR catalyst can be estimated based on for example a stabilised NOx emission level of the exhaust gas leaving the SCR catalyst upon stopped reductant injection, in which condition is can be assumed that NOx emission level of the exhaust gas entering the SCR catalyst equals NOx emission level of the exhaust as leaving the SCR catalyst.

The step of ensuring, that said SCR catalyst NH3 storage level is substantially below the current maximal NH3 storage capacity of said SCR catalyst may be realised by reducing injection of reductant until a NOx level downstream of said SCR catalyst as provided by said exhaust gas sensor is above 50%, specifically above 75%, more specifically above 90% of a NOx level upstream of said SCR catalyst as provided by said additional exhaust gas sensor. During normal operation of a modern SCR catalyst based exhaust aftertreatment system, NOx conversion efficiency is substantially above 70%. Accordingly, the NOx level downstream of said SCR catalyst is normally substantially below 30% of a NOx level upstream of said SCR catalyst.

Consequently, when a NOx level downstream of said SCR catalyst is above 50% of a NOx level upstream of said SCR catalyst, this is a strong indication that the SCR catalyst NH3 storage level is depleted, because otherwise the remaining NH3 in the SCR catalyst would assure a significantly reduced NOx level downstream.

The step of ensuring that said SCR catalyst NH3 storage level is substantially below the current maximal NH3 storage capacity of said SCR catalyst may alternatively be realised by reducing injection of reductant until a rate of change of the output signal of said exhaust gas sensor decreases down below a predefined second threshold value. Upon reducing reductant injection to a sufficient extent, stored ammonia within the SCR catalyst will eventually be converted, and the NOx level downstream of the SCR catalyst will start to increase because insufficient ammonia is provided, for efficient NOx conversion. The rate of change of the output signal of said exhaust gas sensor will thus initially increase along with increased NOx level. The NOx level downstream of the SCR catalyst will eventually stabilise, and the rate of change of the output signal of said exhaust gas sensor will decrease again, eventually down below said predefined second threshold value.

The method may further comprise the step of starting the sequence of method steps by initiating engine operation at a steady state point with respect to NOx emissions reaching said SCR catalyst, and keeping said engine steady state point operation until the end of said recording of said output signal of said exhaust gas sensor. Constant NOx level upstream of SCR catalyst allows the use of a single downstream exhaust gas sensor to be used, and supports the maintenance of a stable exhaust gas temperature.

The method may also comprise the step of further waiting for a predefined time period after initiating engine operation at a steady state point, such that the exhaust gas properties and exhaust aftertreatment system can stabilise.

The method may further comprise the step of providing isothermal exhaust gas conditions at the inlet of said SCR catalyst before initiating said over-injection of reductant. or at least before stopping reductant injection upon registering said increasing NOx+NH3 emission level and an NOx+NH3 emission level exceeding the predefined threshold value. SCR catalyst ammonia storage capacity is normally to a large degree dependent on the temperature of the SCR catalyst, and isothermal exhaust gas conditions at the inlet of said SCR catalyst thus supports a stable SCR catalyst temperature, such that an accurate SCR catalyst diagnose can be determined for a particular temperature level.

A control unit associated with the exhaust aftertreatment system may be configured to control reductant injection by means of a reductant dosing model, and a reductant dosage rate corresponding to said over-injection may be determined by multiplying a dosage rate as provided by said reductant dosing model with an overflow coefficient. The reductant dosage model normally provides the dosage rate that is considered to result in most efficient NOx conversion of the SCR catalyst, Upon multiplying said dosage rate with an overflow coefficient, such as for example 2.0, an increased level of reductant dosage is accomplished. If the overflow coefficient is too high, unreacted liquid reductant may accumulate in the exhaust gas pipe, and if the overflow coefficient is too low, an ammonia-slip catalyst may have sufficient capacity to convert the entire ammonia-slip leaving the SCR catalyst, such that no ammonia-slip can be detected by the exhaust gas sensor installed downstream the combined SCR catalyst and ammonia-slip catalyst.

The increasing NOx+NH3 emission level and an NOx+NH3 emission level exceeding the predefined threshold value may be registered when SNOX_OUT>SNOX_MIN, where SNOX_OUT denotes the current output signal of said exhaust gas sensor, SNOX_MIN denotes an updated minimum exhaust gas sensor output signal recorded during said recording, and K denotes a predefined multiplication factor. This method of determining begin of ammonia-slip provides a fast and reliable identification of start of ammonia-slip, By constantly updating the minimum exhaust gas sensor output signal (SNOX_MIN), the downstream NOx value is allowed to initially sink upon initiation of reductant over-injection, and no predetermined quantitative threshold value is required.

An indication of a minimal or negligible NH3 storage level may be determined when the NOx level as measured by said exhaust gas sensor has reached a predefined percentage level, such as 80%, of the NOx level as measured by said additional exhaust gas sensor, or alternatively, when a predetermined time period has passed after the NOx level as measured by said exhaust gas sensor has reached a specific percentage level, such as 80%, of the NOx level as measured by said additional exhaust gas sensor. The accuracy of the calculated SCR catalyst ammonia storage capacity increases with recording time, but since downstream NOx level somewhat asymptotically approached upstream NOx level, the difference in downstream and upstream NOx levels become more and more insignificant to the final calculated storage capacity. A criteria for ending registering of NOx levels is thus required, and is preferably set to deliver an accurate result without making the diagnose method too time consuming. A single sequence of the method steps may typically, large depending on SCR catalyst temperature and type, take around between 1-10 minutes, and a complete diagnose including several NH3 storage capacity calculations conducted at different SCR catalyst temperatures may typically take around between 10-30 minutes.

An indication of a minimal or negligible NH3 storage level may be determined when a rate of change of the output signal of said exhaust gas sensor has decreased below a predefined third threshold value. Upon stopping or reducing reductant injection, any stored ammonia within the SCR catalyst will eventually be converted, and the NOx level downstream of the SCR catalyst will start to increase because insufficient ammonia is provided for efficient NOx conversion. The rate of change of the output signal of said exhaust gas sensor will thus initially increase. The NOx level downstream of the SCR catalyst will eventually stabilise, and the rate of change of the output signal of said exhaust gas sensor will decrease again. When the reductant injection is completely stopped, the NOx level downstream of the SCR catalyst will stabilise at a level corresponding to the NOx level upstream of the SCR catalyst.

The calculation of said SCR catalyst NH3 storage capacity is based on integrating, preferably from the start to the end of said recording, a difference between the recorded NOx level as measured by said exhaust gas sensor and a constant value corresponding to the recorded. NOx level as measured by said exhaust gas sensor at the end of said recording. During said recording, reductant injection is stopped, and since the ammonia slip due to said over-injection was detected very early, as mention above, substantially zero ammonia slip will be included in said recording. From this, it is clear that the output signal of the exhaust gas sensor completely corresponds to the NOx emission level only, and not due to any ammonia slip. Furthermore, by estimating with good accuracy the amount of converted NOx during said recording, the level of stored ammonia within the SCR catalyst can be derived. For best accuracy, the complete recording, i.e. from the start to the end, should be used. The amount of converted NOx during said recording could be derived by taking the difference between NOx level upstream and downstream of the SCR catalyst. However, when no upstream NOx level information is available, the more or less stabilised downstream NOx level may represent the upstream NOx level.

The method may further comprise the step of recording also an output signal of said additional exhaust gas sensor simultaneously with said recording of said output signal of said exhaust gas sensor. As a consequence, the calculation of said SCR catalyst NH3 storage capacity may be based on integrating the difference between the recorded NOx level as measured by said exhaust as sensor and the recorded NOx level as measured by said additional exhaust gas sensor. According to this configuration, there is thus no need to make any estimate of the upstream NOx level, as previously discussed.

The calculation of said SCR catalyst NH3 storage capacity is preferably further based on a mass or volumetric flow rate of the exhaust gas during; said recording, a NO/NO2 ratio of the exhaust gas entering said SCR catalyst, and a predictive NH3-NO/NO2 reaction model for said SCR catalyst, and a SCR catalyst exhaust gas temperature.

The method may further comprise the step of repeating the sequence of method steps for diagnosing said SCR catalyst at a different isothermal condition for acquiring an improved diagnose of the SCR catalyst.

The SCR catalyst may jointly with a NH3 slip catalyst form a single unit. The NH3 slip catalyst would then be configured to remove unreacted ammonia leaving the SCR catalyst up to a certain level. The exhaust gas sensor is then arranged downstream of said unit, i.e., downstream of said ammonia slip catalyst.

The method may further comprise the step of comparing said calculated SCR catalyst NH3 storage capacity with earlier calculated SCR catalyst NH3 storage capacity, or other type of reference data relating to SCR catalyst NH3 storage capacity.

BRIEF DESCRIPTION OF DRAWINGS

In the detailed description of the invention given below reference is made to the following figure, in which.

DETAILED DESCRIPTION

Various aspects of the invention will hereinafter be described in conjunction with the appended drawings provided to illustrate and not to limit the invention, wherein like designations denote like elements, and variations of the aspects are not restricted to the specific shown aspect, but are applicable on other variations of the invention.

Figure 1:
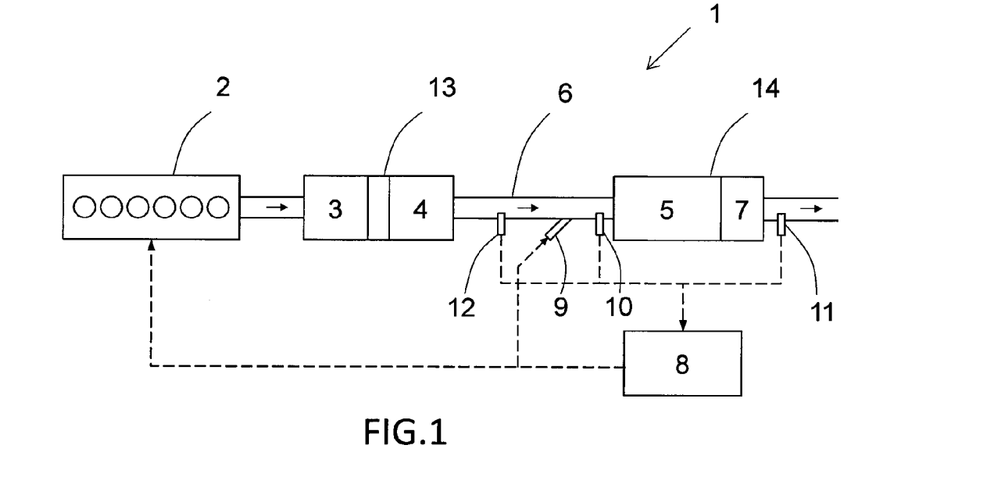
FIG. 1 shows schematically an engine connected with an exhaust aftertreatment system.

FIG. 1 shows schematically an exemplary layout of an exhaust aftertreatment system 1 of a diesel engine 2, in particular for a heavy truck or bus, or the like. The specific, exhaust aftertreatment system 1 shown includes a unit 13 comprising a diesel oxidation catalyst 3 and a particulate filter 4 to reduce the level of carbon monoxide (CO), hydrocarbons (HC), and particulate matter. NOx emission from the engine 2 must also be reduced to comply with regulatory emission standards, and a SCR catalyst 5 is installed along the exhaust gas pipe 6 for this reason. Selective catalytic reduction is a means of converting NOx with the aid of a catalyst into nitrogen (N2) and water (H2O). A reductant, typically urea, is added to the exhaust gas stream upstream of the SCR catalyst 5 by means of an injector 9, and converted to ammonia upon hydrolysis, which ammonia is adsorbed onto the SCR catalyst 5, The SCR catalyst 5 may he of the iron- or copper-based zeolite type, or vanadium-based type. An ammonia-slip catalyst 7 is installed downstream of the SCR catalyst 5, and forms jointly with the SCR catalyst 5 a single unit 14, as is well-known in the prior art. A control unit 8 associated with the exhaust aftertreatment system 1 may be configured to control reductant injection at the injector 9 upstream of the SCR catalyst 5 by means of a reductant dosing model, which may use different parameters as input signals, such as temperature of the exhaust gas entering the SCR catalyst 5 as provided by a temperature sensor 10. Alternatively, a temperature sensor may be provided on each side of the SCR catalyst, and a mean value of these two sensors may be supplied to the control unit 8. An exhaust gas sensor 11 located downstream of the SCR. catalyst 5 is provided to primarily detect the level of NOx emission in the exhaust gas. However, the exhaust gas sensor 11 is cross-sensitive also to ammonia. An additional exhaust gas sensor 12 is preferably installed upstream of the SCR catalyst 5, such that SCR conversion efficiency can be accurately determined.

The inventive method for diagnosing the SCR catalyst 5 of the exhaust aftertreatment system 1 is primarily concerned with obtaining and periodically monitoring, a SCR catalyst ammonia storage capacity during aftermarket time period. The ammonia storage capacity of the SCR catalyst give an indication of the ability of the SCR catalyst 5 to respond to transient changes of the exhaust aftertreatment system 1 which changes may be changes in exhaust gas temperature, or level of NOx emission in the exhaust gas. A high ammonia storage capacity compensates for any incorrect or sub-optimal reductant injection levels, in particular during said transient conditions, due to the adsorbed ammonia content of the SCR catalyst 5. Low ammonia storage capacity results in low level of adsorbed ammonia content, such that regulatory emission standards possibly cannot be complied with.

The SCR ammonia storage capacity cannot be directly measured, and acquiring an estimate of the ammonia storage capacity often requires an dedicated ammonia sensor installed downstream of the SCR catalyst 5, since standard available NOx sensors are cross-sensitive to both NOx and NH3, making it difficult or impossible to draw any accurate conclusions of the NOx level of the exhaust gas downstream of the SCR catalyst 5.

The aim of the invention is to provide a reliable method for acquiring an accurate estimate of the ammonia storage capacity based on the output signal of the exhaust gas sensor 11, and without the need for a dedicated ammonia sensor. The inventive method may alternatively rely also on the output signal of additional exhaust gas sensor 12, The additional gas exhaust sensor 12 is preferably a conventional NOx sensor, and of the same type as downstream exhaust gas sensor 11. The additional gas exhaust sensor 12 is configured to measure the level of NOx present within the exhaust gas entering, said SCR catalyst 5. The additional exhaust gas sensor 12 is installed upstream of the reductant injector 9 to avoid ammonia resulting from the reductant injection to distort the NOx measurement.

Figure 2:
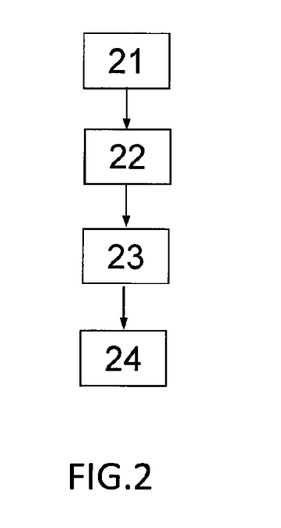
FIG. 2 shows the main method steps of the inventive diagnose.

Below, the inventive method for diagnosing the SCR catalyst 5 of the exhaust aftertreatment system 1 will be disclosed in connection with FIG. 2. The method may start with the a first step 21 of ensuring that a SCR catalyst NH3 storage level is substantially below the current maximal NH3 storage capacity of said SCR catalyst 5. This first step 21 serves to ensure that any ammonia slip downstream of the SCR catalyst, if present, is stopped. Subsequent steps involves reductant over-injection and early identification of begin of ammonia slip, and for this reason, it is vital that any ammonia slip is stopped. It is also important that the SCR catalyst ammonia storage level is reduced from a current maximal NH3 storage capacity to a certain extent, because otherwise the ammonia slip could occur directly upon initiation of the reductant over-injection, making the early identification of ammonia slip less accurate and reliable.

In an exhaust aftertreatment system 1 including the additional exhaust gas sensor 12, the first step 21 may be realised, by reducing injection of reductant until a NOx level as provided by the exhaust gas sensor 11 has increased, to a level above for example 50% of the NOx level as provided by the additional exhaust gas sensor 12. This high downstream NOx level can normally not occur in normal operation of the engine 2 and exhaust aftertreatment system 1 because of the generally high conversion efficiency of the SCR. catalyst 5, However, upon reduced reductant injection rate, the stored ammonia in the SCR catalyst will eventually be exhausted. As a result thereof the NOx conversion efficiency will decrease and the NOx level downstream the SCR catalyst 5 will increase, approaching the NOx level upstream of the SCR catalyst 5, it is of course possible to select other threshold levels for identifying a SCR catalyst NH3 storage level that is substantially below the current maximal NH3 storage capacity of said SCR catalyst 5, for example when the NOx level as provided by the exhaust gas sensor 11 has increased to a level above for example 75%, or more specifically above 90%, of the NOx level as provided by the additional exhaust gas sensor 12.

If the exhaust aftertreatment system 1 cannot rely on the output signal of the additional exhaust gas sensor 12 upstream of the SCR catalyst 5, the first step 21 may be realised by Operating the engine 2 with a reduced reductant injection rate until a rate of change of the output signal of said exhaust gas sensor 11 decreases down below the predefined second threshold. value. Upon reducing the reductant injection rate, the NOx level as provided by the exhaust gas sensor 11 will likely initially be unaffected due to the stored ammonia in the SCR catalyst 5, which stored ammonia will uphold efficient NOx conversion despite reduced reductant injection rate. Said rate of change will thus likely initially remain low or zero. After a certain time however, when the level of stored ammonia becomes smaller and smaller, the NOx conversion efficiency decreases and the NOx value as provided by the exhaust gas sensor 11 consequently starts to increase, leading to increased rate of change of said output signal. Depending on the level of reductant injection, the NOx level as provided by the exhaust gas sensor 11 will eventually stabilise at a certain level, and said rate of change will decrease down to a very low level, or even zero. During said decrease of rate of change, said predefined second threshold value will eventually be reached and the system will conclude that the SCR catalyst NH3 storage level that is substantially below the current maximal NH3 storage capacity of said SCR catalyst 5. According to still a further alternative, the first step 21 may be realised by reducing reductant injection rate until a rate of change of the output signal of said exhaust gas sensor 11 increases above a predefined fourth threshold value, which change of rate, as explained above, result from a nearly exhausted ammonia storage level in the SCR catalyst 5.

All above described alternatives with respect to identifying substantially reduced NH3 storage level rely on some type of affirmative indication. However, even if such affirmative indications ma be preferable, other methods for determining substantially reduced SCR storage level are possible, such as fur example simply waiting for a predetermined time period after entering a reduced reductant injection rate mode, presuming that the ammonia storage level decreases as a result thereof but without verifying this event.

For sake of clarity, reducing the reductant injection rate as described above, the reductant dosage rate is reduced compared with a normal dosage rate, as would have been applied to the specific engine setting, estimated or measured exhaust gas NOx level, exhaust gas temperature, and similar parameters upon which the reductant dosage model is based. The reductant dosage rate may be selected according to the specific situation. The reductant dosage rate may even be reduced down to zero, i.e. completely stopped reduction injection. If for example the dosage model is not configured for the specific engine settings used during the diagnose, reduced injection of reductant may alternatively be provided by choosing in particular fuel injection settings such that elevated NOx emissions are produced, but without increasing the reductant dosage rate correspondingly, thereby artificially ensuring that said NH3 storage level is substantially below the current maximal NH3 storage capacity of said SCR catalyst 5 after a certain time period.

When it is ensured that the SCR catalyst NH3 storage level is substantially below the current maximal NH3 storage capacity of said SCR catalyst, initiation of over-injection of reductant by said injector 9 is commenced according to a second step 22 of the method of the invention. Over-injection of reductant herein refers to setting the reductant dosage rate substantially above the normal dosage rate, as previously defined. For example, the reductant dosage rate may be doubled compared with a normal reductant dosage rate. A multiplication factor, also referred to as overflow coefficient, may advantageously be applied to the normal dosage rate to calculate an increased dosage rate to be used during the over-injection phase. Dosage rate is herein defined as volume of reductant injected per time unit.

A third step 23 of the method is entered upon registering, by said exhaust gas sensor 11, an increasing NOx+NH3 emission level and an NOx+NH3 emission level exceeding the predefined threshold value. As previously discussed, the NOx emission level may initially decrease upon commencing reductant over-injection, or it may initially remain substantially stable. Identification of start of ammonia-slip consequently requires fulfilment of two criteria, namely an increasing NOx+NH3 emission level, as well as a NOx+NH3 emission level exceeding the predefined threshold value. The second criteria alone, i.e. NOx+NH3 emission level exceeding the predefined threshold value may not be sufficient since the NOx+NH3 emission level initially may exceed said predefined threshold value due to initially high NOx emission level. However, the third step aims to detect start of NH3 slip. For this reason, also the criteria of an increasing NOx+NH3 emission level is required to prevent an initially high NOx level to misinterpreted as NH3 slip. The term "NOx+NH3 emission level" herein refers to the summed NOx and NH3 emission level as provided by the exhaust gas sensor 11, since said sensor is cross sensitive to both NOx and NH3.

The increasing, NOx+NH3 emission level and an NOx+NH3 emission level exceeding the predefined threshold value may for example be registered when the following criteria is fulfilled: SNOX_OUT>SNOX_IN X, where SNOX_OUT denotes the current output signal of said exhaust gas sensor 11, i.e. the corresponding to the present summed NOx and NH3 emission levels, SNOX_MIN denotes an updated minimum exhaust gas sensor output signal recorded during said recording, and K denotes a predefined multiplication factor. The multiplication factor may be a constant value, such as for example in the range of 3 to 10. Alternatively, the multiplication factor may be made variable on the current NOx levels such as for example X % of the upstream NOx as measured by the additional exhaust gas sensor 12, or Y % of the downstream NOx as measured by the exhaust gas sensor 11 just before initiating said reductant over-injection of the second step 22. X or Y may for example be in the range of 1% 5%, preferably around 2%. In the beginning of the recording, SNOX_MIN is given the value of the presently measured SNOX_OUT- Thereafter during the recording, SNOX_MIN is given the value of the presently measured SNOX_OUT as soon as SNOX_OUT has a lower value than the value of SNOX_ IN- This procedure ensures that SNOX_IN is constantly updated with the minimal exhaust gas sensor output signal as recorded during said recording.

As a result of entering the third step 23 the method, reductant injection is completely stopped and recording of an output signal of said exhaust gas sensor 11 is started, which recording will continue until an indication of a minimal or negligible NH3 storage level is determined. The recording can for example he conducted using a 1 Hz sampling frequency, and the recorded values of the output signal are stored in a digital storage medium. In a fourth step of the method, which will be discussed more in detail below, the NH3 storage capacity of the SCR catalyst 5 calculated, and the accuracy of the calculated capacity depends on the level of exhaustion of the stored ammonia in the SCR catalyst 5. A higher level of SCR catalyst ammonia exhaustion results in higher accuracy of the calculated ammonia capacity. However, due mainly on time constraints, the recording may have to be terminated before reaching a completely exhausted SCR catalyst ammonia content.

The recording according to the invention will therefore be stopped when an indication of a minimal or negligible NH3 storage level is determined. This indication may be determined in many different ways, and may for example be determined when the NOx level as measured by said exhaust gas sensor 11 has reached a predefined percentage level, such as 80%, of the NOx level as measured by said additional exhaust gas sensor 12. According to an alternative, the indication may be determined when a predetermined time period has passed after the NOx level as measured by said exhaust gas sensor 11 has reached a specific percentage level, such as 80%, of the NOx level as measured by said additional exhaust gas sensor 12. According to yet an alternative, which may be used when the method cannot rely upon the output signal of the additional exhaust gas sensor 12, the indication may be determined when a rate of change of the output signal of said exhaust gas sensor 11 has decreased below the predefined third threshold value. Here, said rate of change is initially zero or at least very low due to the adsorbed ammonia within the SCR catalyst, but as the ammonia storage level diminishes, the downstream NOx level will increase, and the rate of change of the output signal of the exhaust gas sensor 11 will thus also increase, until the downstream NOx level stabilises and the rate of change decreases, and ultimately drops below the predefined third threshold value.

After having stopped the recording, a fourth step 24 of the method is entered, in which a SCR catalyst NH3 storage capacity is calculated based on said recorded output signal. The idea is to calculate the amount of NOx having entered the SCR catalyst 5 and reacted with the stored ammonia therein, and subsequently draw a conclusion about the level of stored ammonia that was available with the SCR catalyst 5. Since the recording started with detection of ammonia-slip, it is assumed that the SCR catalyst 5 was fully charged at begin of the recording. Moreover, the amount of NOx having entered the SCR catalyst 5 and reacted with the stored ammonia is calculated by integrating the difference between the level of NOx having entered the SCR catalyst 5 and the level of NOx having been emitted from the SCR catalyst 5. The integration is preferably initiated directly upon stopping, the over-injection and continues to the end of the recording.

If no measurement of the NOx emission level is available upstream the SCR catalyst 5, then the upstream NOx level must be estimated to perform the calculation. One possibility is to assume that the recorded NOx level as measured by the exhaust gas sensor 11 at the end of the recording adequately represents the NOx emission level upstream of the SCR catalyst 5, because the NOx conversion efficiency of the SCR catalyst 5 is assumed to have dropped to at insignificant value at the end of the recording. Then the difference between the recorded NOx level as measured by the exhaust gas sensor 11 and a constant value corresponding to the recorded NOx level as measured by the exhaust gas sensor 11 at the end of the recording could be integrated. As an alternative, in case the ammonia content of the SCR catalyst 5 was substantially exhausted during the first step 21 a recorded value of the gas exhaust sensor at the end of the first step 21 could adequately represent the NOx emission level upstream of the SCR catalyst 5 during the following recording phase.

When an output signal of the additional exhaust gas sensor 12 is available, this output signal should be recording simultaneously with the recording of the output signal of the exhaust gas sensor 11. This simplifies calculation of the SCR catalyst ammonia storage capacity because the calculation may then be based on integration of the difference between the recorded NOx level, as measured by the exhaust gas sensor and the recorded NOx level as measured by the additional exhaust gas sensor 12.

For all different alternatives of calculating the amount of NOx having entered the SCR catalyst 5 and reacted with the stored ammonia, the final calculation of the NH3 storage capacity requires estimation of a number of parameters, such as mass or volumetric flow rate of the exhaust gas during the recording, a NO/NO2 ratio of the exhaust gas entering the SCR catalyst 5, a predictive NH3-NO/NO2 reaction model for the SCR catalyst 5, molars mass of NH3, NO and NO2, the SCR catalyst exhaust gas temperature during, the recording, etc.

For example, assuming that only the fast reaction is happening (2 NH3+NO+NO2→2 N2+2 H2O), and that the upstream NOx gas consists of 50% NO2 and 50% NO, then NH3 (g/1)=NH3(g)/Volume of SCR catalyst (liters) for a certain temperature can be calculated, where:
NH3 (g/l) denotes SCR catalyst ammonia storage capacity in grams/liters;
NH3(g)=(17/46)*Integral (upstream NOx level−downstream NOx level) during the recording;
NH3: 17 g/mol
NO2/NO: 46 g/mol.

The method may further comprise a preparation step ahead of the first step 21 discussed above, which preparation step comprising initiation of engine operation at a steady state point with respect to NOx emissions reaching the SCR catalyst 5, and keeping said engine steady state point operation until the end of said recording of said output signal of said exhaust gas sensor 5. The method may in addition comprise the step of further waiting for a predefined time period after initiating engine operation at a. steady state point in the preparation step. This waiting time is configured to allow the exhaust gas properties and exhaust aftertreatment system 1 to stabilise before proceeding with the first step 21. Similarly, the method may further or alternatively comprise the step of providing isothermal exhaust gas conditions at the inlet of said SCR catalyst 5 before initiating said over-injection of reductant, or at least before stopping reductant injection upon registering said increasing NOx+ NH3 emission level and an NOx+NH3 emission level exceeding the predefined threshold value. Isothermal exhaust gas conditions during the diagnose is important o generate an accurate calculation of the ammonia storage capacity.

For providing an improved diagnose of the SCR catalyst 5, ammonia storage capacity calculations should be conducted at several different SCR catalyst operating temperatures. The method may thus comprise the step of repeating the sequence of method steps 21-24 for diagnosing the SCR catalyst at different isothermal conditions.

For the purpose of tracking aging and continuous degradation of the SCR catalyst 5 over time, the monitoring of the SCR catalyst ammonia storage capacity over time may give a good and relevant diagnose of the SCR catalyst 5, and consequently also a good indication to what extent the aftertreatment system 1 complies with regulatory NOx emission standards. The method may thus advantageously further comprise the step of comparing the last calculated SCR catalyst NH3 storage capacity with earlier calculated and stored SCR catalyst NH3 storage capacities for identifying SCR catalyst degradation etc. Alternatively, or in addition, the last calculated SCR catalyst NH3 storage capacity may be compared with other type of reference data relating to SCR catalyst NM storage capacity, such as typical SCR catalyst data, preferably taking into account the relevant age of the SCR catalyst 5.

Figure 3:
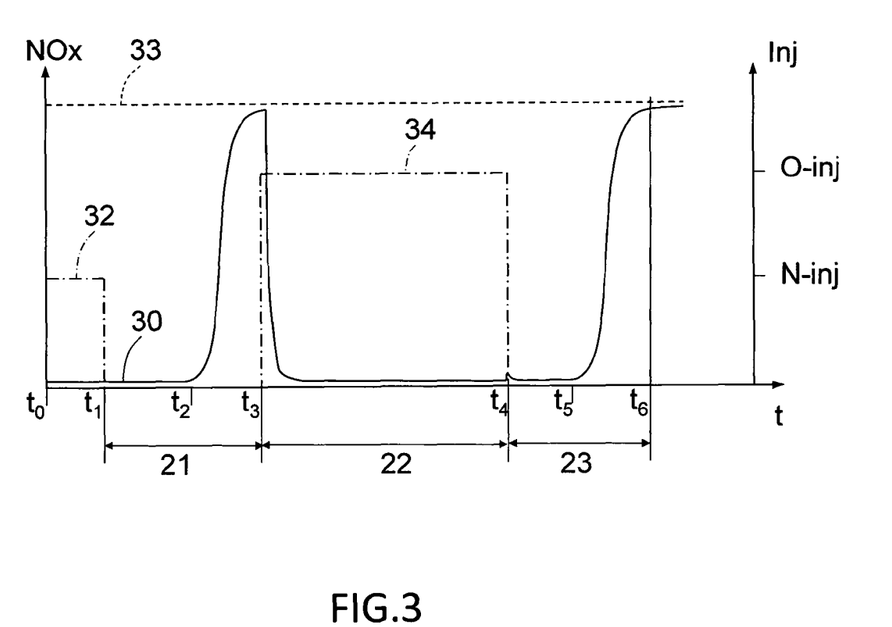
FIG. 3 shows a schematic diagram of output signals of the exhaust gas sensor and the additional exhaust gas sensor, as well as the reductant injection levels.

The above described method steps of the method of diagnosing the SCR catalyst 5 are further illustrated by means of the schematic diagram of FIG. 3, where the X-axis denotes time (t), the left Y-axis denotes upstream exhaust gas NOx level as provided by the additional exhaust gas sensor 12 and downstream exhaust gas NOx+NH3 level as provided by the exhaust gas sensor 11, and the right Y-axis denotes reductant injection rate. At time point to, the reductant injection rate 32 is set at a normal injection level N-inj, which results in an optimal SCR conversion efficiency based on current NOx level 33 upstream of the SCR catalyst as provided by the additional exhaust gas sensor 12. At the same time, the NOx+NH3 emission level 30 downstream the SCR catalyst 5 as measured by the exhaust gas sensor 11 is very low, maybe just around 10 parts per million (ppm), which for example corresponds to about 3-6% of the NOx emission level 33 upstream of the SCR catalyst 5, depending on said NOx conversion efficiency. At this stage the engine 2 is operated at a steady state point with respect to NOx level 33 upstream the SCR catalyst 5, and this upstream NOx level 33 is kept during the entire diagnose, and isothermal exhaust gas conditions is provided at the inlet of said SCR catalyst 5. Herein, isothermal exhaust gas conditions encompass a certain deuce of exhaust gas temperature variation around to target temperature, such as for example +/-5%.

There is no quantitative information of the current SCR catalyst NH3 storage level hut the control unit strives to keep the NH3 ammonia storage level on an appropriate level using for example a SCR catalyst storage level model.

At time ti, the control unit 8 has commanded reduced reductant injection rate in order to ensure that the SCR catalyst NH3 storage level starts to approach a value substantially below the current maximal NH3 storage capacity of said SCR catalyst 5. Between the time ti and t.2, the downstream NOx level remains at a low level by means of the stored ammonia within the SCR catalyst 5. About time t2, the downstream NOx level starts to increase due to a nearly exhausted ammonia storage level of the SCR catalyst 5.

At time t3, it is ensured that the SCR catalyst NH3 storage level is substantially below the current maximal NH3 storage capacity of said SCR catalyst 5. This is in the illustrated embodiment realised when the NOx level 30 downstream of the SCR catalyst 5 is above around 90% of the NOx level upstream of the SCR catalyst 5, and the second step 22 of the method, involving, charging of the SCR catalyst 5 with ammonia is commenced. The SCR catalyst 5 is nearly free of stored ammonia, and is now charged, from time t3 onwards, by reductant over-injection. The SCR catalyst 5 charging is conducted under isothermal conditions, with an exhaust as input flow of a predefined and temporarily constant magnitude, and constant ammonia input concentration, as indicated by the constant reductant over-injection level 34, which may be set to about 200% of the normal injection level 32. The SCR catalyst 5 receives excessive level of ammonia between time t3 and U, and part of the supplied ammonia is stored in the SCR catalyst 5. As a result of the reductant over-injection, the NOx conversion efficiency increases again, and the illustrated downstream NOx level 30 sinks to a level close to the downstream NOx level 30 detected before time ti. The output signal of the exhaust gas sensor 11 is continuously monitored to identify the start of the ammonia slip of the SCR catalyst 5. The ammonia slip will occur due to the reductant over-injection level 34, which is selected such that the ammonia slip catalyst 7 cannot that convert the entire level of ammonia that will reach the ammonia slip catalyst 7 when the SCR catalyst 5 is fully, or at least nearly fully charged with ammonia. At around time, the SCR catalyst 5 is saturated and a slightly increasing NOx+NH3 emission level and an NOx+NH3 emission level exceeding the predefined threshold value is registered, and the reductant over-injection 34 is stopped and the recording of the output signal of both the exhaust gas sensor 11 and the additional gas exhaust sensor 12 is commenced.

Due to the careful preparation for identifying the start of the ammonia slip, the detection can be realised at a very early stage, for example down below an output emission level of 50 ppm as provided by the exhaust gas sensor 11. Just to give an example, upstream NOx level 33 may be about 400 ppm as provided by the additional exhaust gas sensor 12, and downstream emission level 30 just before time I may be about 10 ppm. This emission level is here considered to represent NOx emission level downstream of the SCR catalyst 5 because no ammonia slip is still detected. Detection of start of ammonia slip is made when emission level as provided by the exhaust gas sensor 11 has increased to about 20 ppm, from which 10 ppm is assumed to correspond to the ammonia slip emission level. From this example, it is clear that the ammonia slip itself will influence the finally calculated ammonia storage capacity to a very small and insignificant extent.

About time t5, the downstream NOx level starts to increase due to a nearly exhausted ammonia storage level of the SCR catalyst 5. The recording is stopped at time t& upon receiving an indication that a minimal or negligible SCR catalyst NH3 storage level is attained, because the NOx level as measured by said exhaust gas sensor has reached about 90% of the NOx level as measured by said additional exhaust gas sensor 11. Consequently, the recording is stopped, the third step 23 is completed, and the fourth step of calculating the SCR catalyst NH3 storage capacity is performed.

For sake of clarity, the first, second and third steps 21, 22, 23 of the diagnose method are also illustrated in FIG. 3.

The term downstream herein refers to a position downstream of the SCR catalyst at the location of the exhaust gas sensor. The term upstream herein refers to a position upstream of the SCR catalyst, and more particularly at the location of the additional exhaust gas sensor if such a sensor is provided. Reference signs mentioned in the claims should not be seen as limiting the extent of the matter protected by the claims, and their sole function is to make claims easier to understand. As will be realised, the invention is capable of modification in various obvious respects, all without departing from the scope of the appended claims. Accordingly, the drawings and the description thereto are to he regarded as illustrative in nature, and not restrictive.

The invention claimed is:

1. A method for determining an ammonia (NH3) storage capacity of a selective catalytic reduction (SCR) catalyst of an exhaust aftertreatment system of an internal combustion engine, wherein the exhaust aftertreatment system comprises a SCR catalyst, an reductant injector arranged upstream of the SCR catalyst for injecting a reductant into an exhaust gas, and an exhaust gas sensor arranged downstream of the SCR catalyst, which exhaust gas sensor being cross-sensitive to nitrogen oxide (NOx) and NH3 present within the exhaust gas leaving the SCR catalyst, wherein the method comprises the steps of:

ensuring that a SCR catalyst NH3 storage level is substantially below a current maximal NH3 storage capacity of the SCR catalyst;

initiating over-injection of reductant by the injector;

stopping reductant injection in response to registering, by the exhaust gas sensor, an increasing NOx+NH3 emission level and an NOx+NH3 emission level exceeding a predefined threshold value, and when the reduction injection is stopped recording an output signal of the exhaust gas sensor until an indication of a minimal negligible SCR catalyst NH3 storage level is determined; and calculating a SCR catalyst NH3 storage capacity on a basis of the recorded output signal, wherein the storage capacity is calculated by integrating a difference between an estimated or recorded level of nitrogen oxide (NOx) having entered the SCR catalyst and a recorded level of nitrogen oxide (NOx) having been emitted from the SCR catalyst.

2. The method according to 1, comprising providing the exhaust aftertreatment system with an additional exhaust gas sensor arranged upstream of the reductant injector and configured to measure a level of NOx present within the exhaust gas entering the SCR catalyst.

3. The method according to claim 2, wherein the step of ensuring that the SCR catalyst NH3 storage level is substantially below the current maximal NH3 storage capacity of the SCR catalyst is realised by reducing injection of reductant until a NOx level downstream of the SCR catalyst as provided by the exhaust gas sensor is above 50% of a NOx level upstream of the SCR catalyst as provided by the additional exhaust gas sensor.

4. The method according to claim 3, wherein injection of reductant is reduced down to zero.

5. The method according to claim 2, wherein an indication of a minimal or negligible NH3 storage level is determined
when the NOx level as measured by the exhaust gas sensor has reached a predefined percentage level; or
when a predetermined time period has passed after the NOx level as measured by the exhaust gas sensor has reached a specific percentage level.

6. The method according to claim 2, comprising recording an output signal of the additional exhaust gas sensor simultaneously with the recording of the output signal of the exhaust gas sensor.

7. The method according to claim 6, wherein the calculating of a SCR catalyst NH3 storage capacity is based on integrating the difference between a recorded NOx level as measured by the exhaust gas sensor and the recorded NOx level as measured by the additional exhaust gas sensor.

8. The method according to claim 1, wherein the step of ensuring that the SCR catalyst. NH3 storage level is substantially below the current maximal NH3 storage capacity of the SCR catalyst is realised by reducing injection of reductant until a rate of change of the output signal of the exhaust gas sensor decreases down below a predefined second threshold value.

9. The method according to claim 1 comprising, starting the method by initiating engine operation at a steady state point with respect to NOx emissions reaching the SCR catalyst, and keeping the engine steady state point operation until the end of the recording of the output signal of the exhaust gas sensor.

10. The method according to claim 9, comprising further waiting for a predefined time period after initiating engine operation at a steady state point, such that the exhaust gas properties and exhaust aftertreatment system can stabilise.

11. The method according to claim 1, comprising providing isothermal exhaust gas conditions at an inlet of the SCR catalyst before initiating the over-injection of reductant by the injector, or at least before stopping reductant injection upon registering an increasing NOx+NH3 emission level and an NOx+NH3 emission level exceeding the predefined threshold value.

12. The method according to claim 1, wherein a control unit associated with the exhaust aftertreatment system is configured to control reductant injection by means of a reductant dosing model, and a reductant dosage rate corresponding to the over-injection is determined by multiplying a dosage rate as provided by the reductant dosing model with an overflow coefficient.

13. The method according, to claim 1, wherein an increasing NOx+NH3 emission level and an NOx+NH3 emission level exceeding the predefined threshold value is registered when SNOx_OUT>SNOx_MIN x K, where SNOx_OUT denotes a current output signal of the exhaust gas sensor, SNOx_MIN denotes an updated minimum exhaust gas sensor output signal recorded during the recording, and K denotes a predefined multiplication factor.

14. The method according to claim 1, wherein an indication of a minimal or negligible NH3 storage level is determined when a rate of change of the output signal of the exhaust gas sensor has decreased below a predefined third threshold value.

15. The method according to claim 1, wherein the calculating of a SCR catalyst NH3 storage capacity is based on integrating a difference between a recorded NOx level as measured by the exhaust gas sensor and a constant value corresponding, to the recorded NOx level as measured by the exhaust gas sensor at the end of the recording.

16. The method according to claim 1, wherein the calculating of a SCR catalyst NH3 storage capacity is further based On mass or volumetric flow rate of the exhaust gas during, the recording, a NO/NO2 ratio of the exhaust gas entering the SCR catalyst, and a predictive NH3-NO/NO2 reaction model for the SCR catalyst, and a SCR catalyst exhaust gas temperature.

17. The method according to claim 1, comprising repeating the method steps at a different isothermal condition for acquiring an improved diagnose of the SCR catalyst.

18. The method according to claim 1, wherein the SCR catalyst and a NH3 slip catalyst jointly form a single unit which ammonia slip catalyst is configured to remove unreacted ammonia leaving the SCR catalyst, wherein the exhaust gas sensor is arranged downstream of the ammonia slip catalyst.

19. The method according to claim 1, comprising comparing the calculated SCR catalyst NH3 storage capacity with earlier calculated SCR catalyst NH3 storage capacity, or other type of reference data relating to SCR catalyst NH3 storage capacity.

* * * * *